United States Patent
Saito et al.

(10) Patent No.: US 12,315,188 B2
(45) Date of Patent: May 27, 2025

(54) IMAGE PROCESSING DEVICE AND IMAGE PROCESSING METHOD

(71) Applicant: Panasonic Intellectual Property Management Co., Ltd., Osaka (JP)

(72) Inventors: Kosuke Saito, Osaka (JP); Takeshi Hamasaki, Osaka (JP); Yoshiaki Kanamori, Kyoto (JP); Erika Iwase, Shiga (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 354 days.

(21) Appl. No.: 17/799,590

(22) PCT Filed: Feb. 12, 2021

(86) PCT No.: PCT/JP2021/005376
§ 371 (c)(1),
(2) Date: Aug. 12, 2022

(87) PCT Pub. No.: WO2021/172060
PCT Pub. Date: Sep. 2, 2021

(65) Prior Publication Data
US 2023/0065612 A1  Mar. 2, 2023

(30) Foreign Application Priority Data

Feb. 27, 2020  (JP) ................... 2020-032402

(51) Int. Cl.
G06T 7/73 (2017.01)
G06T 7/11 (2017.01)
G06T 7/60 (2017.01)

(52) U.S. Cl.
CPC ............ *G06T 7/73* (2017.01); *G06T 7/11* (2017.01); *G06T 7/60* (2013.01)

(58) Field of Classification Search
CPC ..... G06T 7/73; G06T 7/11; G06T 7/60; G06T 2207/10004; G06T 2207/30088;
(Continued)

(56) References Cited

U.S. PATENT DOCUMENTS 7,477,782 B2 * 1/2009 Qureshi ............... G06T 7/0012
606/187
2014/0276958 A1 * 9/2014 Zhang .................. A61B 90/37
382/128
(Continued)

FOREIGN PATENT DOCUMENTS

JP   03-218735 A   9/1991
JP   2006-181100 A   7/2006
(Continued)

OTHER PUBLICATIONS

Extended European Search Report dated Jul. 17, 2023 issued in the corresponding European Patent Application No. 21761643.2.
(Continued)

*Primary Examiner* — Tom Y Lu
(74) *Attorney, Agent, or Firm* — Rimon P.C.

(57) ABSTRACT

An image processing device includes: an obtaining unit configured to obtain an image including at least one body hair; and an analyzing unit configured to analyze the image to output information indicating an orientation of the at least one body hair included in the image.

7 Claims, 4 Drawing Sheets

(58) Field of Classification Search
CPC . A61B 5/1072; A61B 2576/00; A61B 5/1079; A61B 5/448
See application file for complete search history.

(56) References Cited

U.S. PATENT DOCUMENTS

| | | | | |
|---|---|---|---|---|
| 2016/0324586 | A1* | 11/2016 | Zingaretti | A61B 17/3468 |
| 2017/0178336 | A1* | 6/2017 | Tu | G06F 18/24 |
| 2017/0333432 | A1* | 11/2017 | Sinclair | A61K 31/522 |
| 2018/0184968 | A1* | 7/2018 | Kasprzak | G06T 7/0012 |

FOREIGN PATENT DOCUMENTS

| | | |
|---|---|---|
| JP | 2009-284124 A | 12/2009 |
| JP | 2010-227222 A | 10/2010 |
| JP | 6444152 B2 | 12/2018 |
| WO | 2018/017811 A1 | 1/2018 |

OTHER PUBLICATIONS

International Search Report issued on Apr. 20, 2021 in International Patent Application No. PCT/JP2021/005376, with English translation.

* cited by examiner

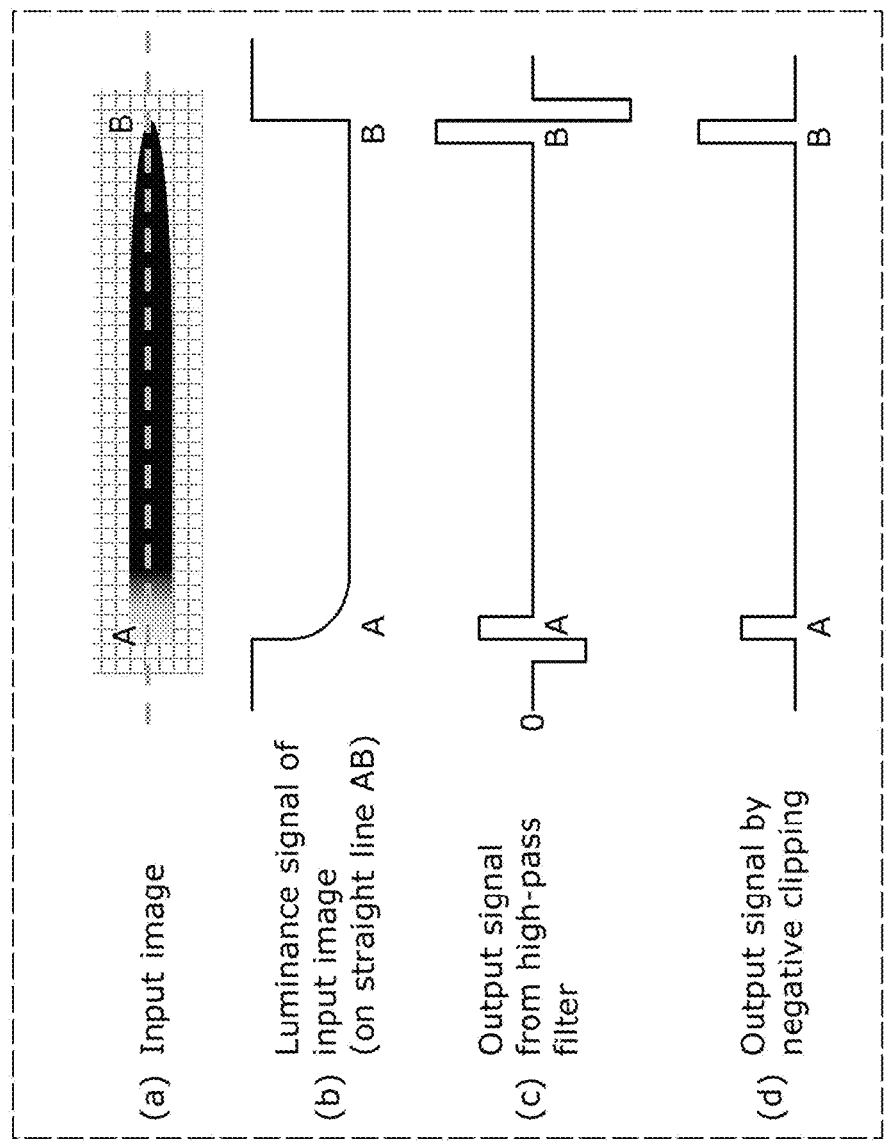

IMAGE PROCESSING DEVICE AND IMAGE PROCESSING METHOD

CROSS-REFERENCE OF RELATED APPLICATIONS

This application is the U.S. National Phase under 35 U.S.C. § 371 of International Patent Application No. PCT/JP2021/005376, filed on Feb. 12, 2021, which in turn claims the benefit of Japanese Patent Application No. 2020-032402, filed on Feb. 27, 2020, the entire disclosures of which Applications are incorporated by reference herein.

TECHNICAL FIELD

The present disclosure relates to an image processing device and an image processing method. In particular, the present disclosure relates to an image processing device and an image processing method that analyze an image of body hair.

BACKGROUND ART

Conventionally, a technique of analyzing body hair have been proposed (see Patent Literature (PTL) 1). PTL 1 proposes a method for recording an image of the scalp and measuring a hair growth rate, trichogram, a hair diameter, etc. from the recorded image of the scalp.

CITATION LIST

Patent Literature

[PTL 1] Japanese Unexamined Patent Application Publication No. 3-218735

SUMMARY OF INVENTION

Technical Problem

However, although PTL 1 provides information about growing hair, PTL 1 does not provide practical information about body hair, such as information for eliminating unshaved hair when body hair is shaved using an electric razor.

In view of the above, the present disclosure provides an image processing device and an image processing method that can provide practical information about body hair.

Solution to Problem

In order to achieve the above, an image processing device according to one aspect of the present disclosure includes: an obtaining unit configured to obtain an image including at least one body hair; and an analyzing unit configured to analyze the image. The analyzing unit is configured to output information indicating an orientation of the at least one body hair included in the image.

In order to achieve the above, an image processing method according to one aspect of the present disclosure includes: obtaining an image including at least one body hair; and analyzing the image to output information indicating an orientation of the at least one body hair included in the image.

Advantageous Effects of Invention

The image processing device and the image processing method according to the present disclosure are effective to obtain practical information about body hair.

BRIEF DESCRIPTION OF DRAWINGS

FIG. 5 is a diagram showing an example of image processing in each step in FIG. 4.

DESCRIPTION OF EMBODIMENTS

An embodiment will be described in detail below, with reference to the drawings. However, description detailed more than necessary may be omitted. For example, detailed description of well-known matters or repeated description of the substantially same configurations may be omitted. This is to avoid unnecessarily redundant description and facilitate the understanding of a person skilled in the art.

It should be noted that the inventors have provided the accompanying drawings and following description in order to facilitate sufficient understanding of the present disclosure by a person skilled in the art, and thus are not intended to limit the subject matters of the claims.

Embodiment

Hereinafter, an embodiment will be described with reference to FIG. 1 through FIG. 5.

[1. Configuration]

Figure 1:
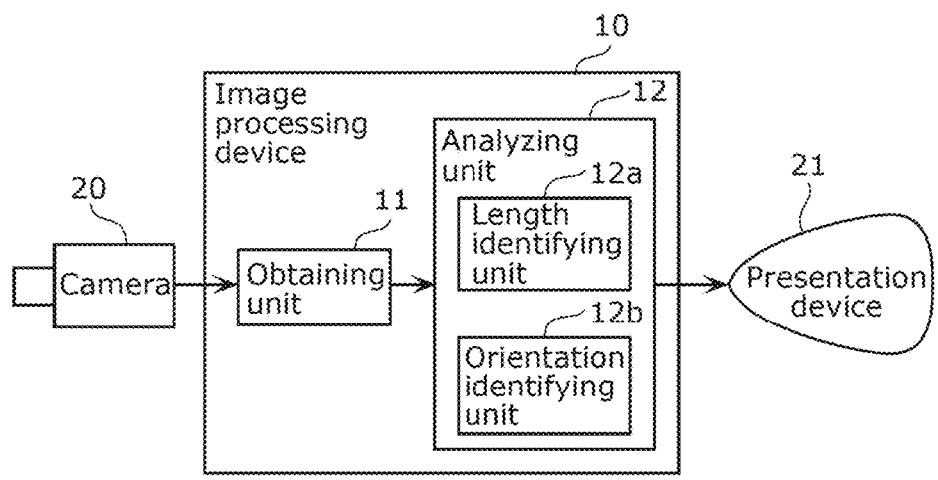
FIG. 1 is a block diagram illustrating a configuration of an image processing device according to an embodiment.

FIG. 1 is a block diagram illustrating a configuration of image processing device 10 according to an embodiment. Note that, the figure also illustrates camera 20, such as a digital camera, and presentation device 21, such as a display, which are used by being connected to image processing device 10.

Image processing device 10 generates practical information about body hair from an input image, and includes obtaining unit 11 and analyzing unit 12. Note that image processing device 10 can be achieved not only by a device including a dedicated electronic circuit, but also by a general-purpose platform, such as a personal computer (PC), a tablet terminal, or a smartphone, and a program to be executed on such a platform.

Obtaining unit 11 obtains, from camera 20, an image that includes at least one body hair growing on a body. Obtaining unit 11 is, for example, a communication interface, such as High-Definition Multimedia Interface (HDMI) (registered trademark).

Note that the image may include image data, image signals, and image information. Moreover, it is sufficient that the image includes an image of at least one body hair, and may include an image of more than one body hairs. In addition, it is sufficient that the image includes at least an image of body hair, and may include information about surroundings of body hair, such as the skin on which the body hair grows.

Analyzing unit 12 analyzes the image obtained by obtaining unit 11 to output information to presentation device 21 indicating the length of at least one body hair and the orientation of the at least one body hair included in the image. Analyzing unit 12 may be achieved by, for example, a microcomputer including a processor, a program executed by the processor, memory, an input/output circuit, etc, Analyzing unit 12 includes length identifying unit 12a and orientation identifying unit 12b.

Length identifying unit 12a analyzes the image obtained by obtaining unit 11 to identify the length of the at least one body hair included in the image, and outputs, to presentation device 21, information indicating the length identified. More specifically, length identifying unit 12a performs, on the obtained image, a process of enhancing contrast, a process of extracting the outline of the body hair, and a process of calculating a bounding box to identify the length of each body hair.

Orientation identifying unit 12b analyzes the image obtained by obtaining unit 11 to output, to presentation device 21, information indicating the orientation of the at least one body hair included in the image. More specifically, orientation identifying unit 12b recognizes at least one of a root or a tip of the at least one body hair included in the obtained image to identify the orientation of each body hair. Specifically, orientation identifying unit 12b analyzes a change in luminance at each of both ends including one end and the other end of at least one body hair included in the image, and determines that an end having a larger change in luminance among the both ends is the tip of the at least one body hair. Here, orientation identifying unit 12b uses a high-pass filter to analyze a change in luminance at one end and the other end of the at least one body hair. Orientation identifying unit 12b recognizes an end having a larger value obtained by applying the high-pass filter among the both ends as the tip of the body hair. Note that orientation identifying unit 12b identifies the orientation of the body hair in an area enclosed by a bounding box calculated by length identifying unit 12a.

Note that orientation identifying unit 12b may identify the orientation of a body hair by analyzing a change in luminance at each of both ends of the body hair and determining that an end having a smaller change in luminance among the both ends is the root of the body hair.

[2. Operation]

Operation of image processing device 10 configured as described above will be described below. Note that, in FIG. 3, an analysis example is given in which an unshaved beard that remains after shaving is used as an example of body hair, and an image obtained by capturing the unshaved beard is analyzed. Operation of length identifying unit 12a and orientation identifying unit 12b included in analyzing unit 12 will be described in detail below.

[2-1. Operation of Length Identifying Unit]

First, operation of length identifying unit 12a included in analyzing unit 12 will be described.

Figure 2:
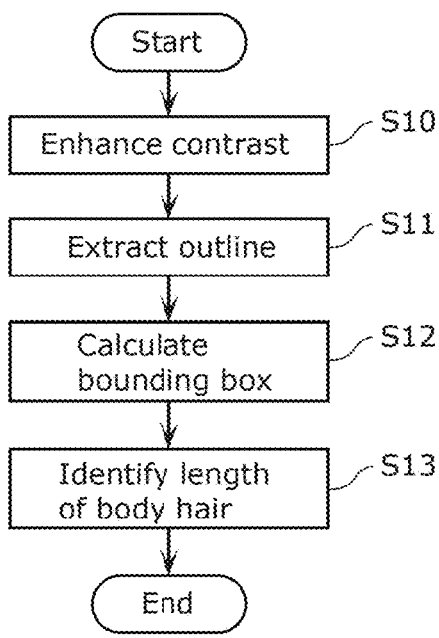
FIG. 2 is a flowchart illustrating operation of a length identifying unit of an analyzing unit included in the image processing device according to the embodiment.
Figure 3:
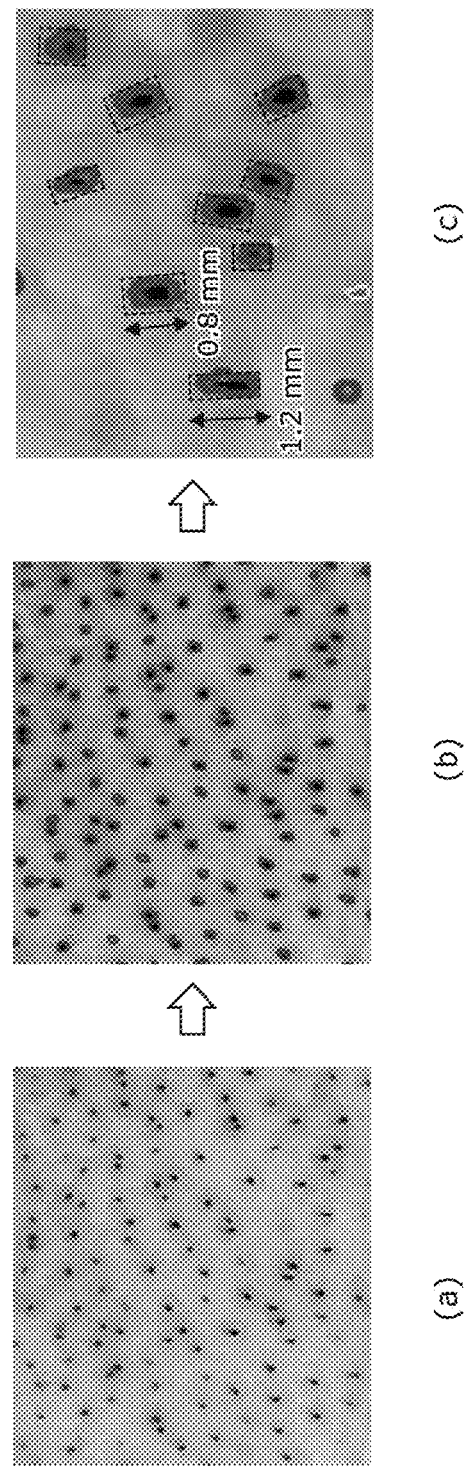
FIG. 3 is a diagram showing an example of mage processing in each step in FIG. 2.

FIG. 2 is a flowchart illustrating operation of length identifying unit 12a of analyzing unit 12 included in image processing device 10 according to the present embodiment, FIG. 3 is a diagram showing an example of image processing in each step in FIG. 2. Moreover, FIG. 3 shows images of a beard as an example of body hair, More specifically, (a) through (c) in FIG. 3 respectively show an exemplary image obtained by enhancing contrast (S10), an exemplary image obtained by extracting outlines (S11), and an exemplary image obtained by calculating bounding boxes (S12) in FIG. 2.

First, length identifying unit 12a performs a process of enhancing contrast on the image of the body hair obtained by obtaining unit 11 (S10 in FIG. 2). For example, length identifying unit 12a increases luminance contrast by performing gradation conversion on the luminance of each pixel in the image to increase the number of output gradations relative to the number of input gradations. As a result, an image having a high contrast as shown in (a) in FIG. 3 is obtained. Note that, fine noise such as irregularities on the skin may be removed by applying a low-pass filter to the image before or after this contrast enhancement.

Subsequently, length identifying unit 12a performs outline extraction on the image obtained in step S10 (S11 in FIG. 2). More specifically, length identifying unit 12a binarizes (blackening/whitening) the image obtained in step S10 by outputting a white pixel when the luminance difference between a target pixel and the surrounding pixels is greater than or equal to a threshold, and outputting a black pixel when the luminance difference between the target pixel and the surrounding pixels is less than the threshold. After that, expansion and contraction processing is performed to remove fine noise. Note that the expansion and contraction processing is to perform expansion processing to replace a target pixel with a white pixel when any white pixel is present around the target pixel, and perform contraction processing to replace the target pixel with a black pixel when any black pixel is present around the target pixel. This outline extraction gives an image indicating the outlines of areas of the individual hairs of the beard, as shown in (b) in FIG. 3.

Subsequently, length identifying unit 12a calculates a bounding box for each area whose outline has been extracted in the image obtained in step S11 (S12 in FIG. 2). Specifically, length identifying unit 12a calculates a bounding box for each area whose outline has been extracted, such that each of the four sides contacts the extracted outline of the body hair. However, the method of calculating the bounding box is not limited to this method, and any other method is also possible as long as a quadrilateral that covers the outline of the body hair can be calculated to estimate the length of the body hair. Moreover, examples of the quadrilateral include squares as well as rectangles. Note that, in this step, a quadrilateral whose corners are all right angles is calculated because such a quadrilateral is more convenient for identifying a length and calculating a change in luminance. A shape different from the quadrilateral may be calculated if such a shape does not interfere with identification of a length or an orientation. This process produces an image showing quadrilaterals that each circumscribe the area of the individual hair of the beard, as shown in (c) in FIG. 3.

Length identifying unit 12a calculates the length of a long side of each of the bounding boxes calculated in step S12 to identify the length of each body hair (S13 in FIG. 2). To identify the length of a long side, the long side is used as the hypotenuse of a right triangle including two sides extending in perpendicular directions in which the pixels are arranged. The lengths of the two perpendicular sides of the right triangle are calculated (each length=number of pixels×pixel pitch). The length of the long side, which is the hypotenuse, is calculated using the Pythagorean theorem.

In this way, the length of each body hair left unshaved by an electric razor is identified from the captured image as practical information about the body hair. Therefore, a user who has obtained this practical information can immediately know which part on the body should be shaved in preference to other parts so that body hair can be shaved efficiently and cleanly,

[2-2. Operation of Orientation Identification Unit]

Next, operation of orientation identifying unit 12b included in analyzing unit 12 will be described.

Figure 4:
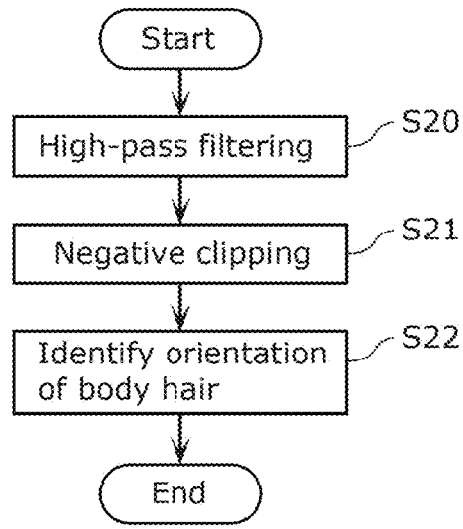
FIG. 4 is a flowchart illustrating operation of an orientation identifying unit of the analyzing unit included in the image processing device according to the embodiment.

FIG. 4 is a flowchart illustrating operation of orientation identifying unit 12b of analyzing unit 12 included in image processing device 10 according to the present embodiment. FIG. 5 is a diagram showing an example of image processing in each step in FIG. 4. More specifically, (a) through (d) in FIG. 5 respectively show an image to be processed ("input image"), a luminance signal of the input image (on the straight line AB), a result of high-pass filtering (S20) in FIG. 4, and a result of negative clipping (S21) in FIG. 4.

Orientation identification unit 12b identifies the orientation of the body hair in each image enclosed by the bounding box calculated by length identifying unit 12a (i.e., each image of the area enclosed by the bounding box in the original image enclosed by the bounding box). The image enclosed by the bounding box has, for example, as shown in (a) in FIG. 5, a gradation that gradually changes from white to black from the root ("A") toward the tip of the body hair. At the tip of the body hair ("B"), there is a large difference in luminance between the area within the outline and the area outside the outline. In other words, unlike the tip, the root of the body hair goes under the skin, and therefore the contrast between the hair and the skin decreases. Orientation identifying unit 12b uses such a feature of the image at the root and the tip of the body hair to identify the orientation of the body hair. Note that (b) in FIG. 5 shows a luminance signal in the longitudinal direction (on straight line AB) of the body hair.

Moreover, it is sufficient that the root of a body hair includes at least part of the body hair covered by the skin and part of the body hair exposed from the skin.

Note that orientation identifying unit 12b may identify the orientation of the body hair in an identification range extended in the longitudinal direction of the bounding box from the image enclosed by the bounding box calculated by length identifying unit 12a. Even when a side of the bounding box calculated by length identifying unit 12a is located at the tip of the body hair or at the border between the root of the body hair and the skin, it is possible to include part of the skin in addition to the tip and the root of the body hair by extending the identification range in the longitudinal direction of the bounding box. This makes it easier to identify the orientation of a body hair, using the gradual change in luminance that appears at the root of a body hair because the root of a body hair goes under the skin.

First, orientation identifying unit 12b applies a high-pass filter to the original image enclosed by a bounding box as shown in (a) in FIG. 5 (S20 in FIG. 4). Specifically, orientation identifying unit 12b applies a high-pass filter having a transfer function expressed as $(1-2z^{-1}+z^{-2})/4$ to the luminance signal on the straight line AB shown in (b) in FIG. 5. As a result, an output signal shown in (c) in FIG. 5 is obtained.

Subsequently, orientation identifying unit 12b performs negative clipping on the output signal shown in (c) in FIG. 5 (S21 in FIG. 4). Specifically, orientation identifying unit 12b replaces a negative value with zero in the output signal shown in (c) of FIG. 5. As a result, an output signal shown in (d) in FIG. 5 is obtained.

Subsequently, orientation identifying unit 12b identifies the orientation of a body hair (here, a hair of a beard) by recognizing, in the output signal shown in (d) in FIG. 5, an end where a high peak appears (here, "B") as the tip of the body hair, and an end where a low peak appears (here, "A") as the root of the body hair (S22 in FIG. 4). Orientation identifying unit 12b then attaches information indicating a root to the end that is recognized as the root of the body hair, and attaches information indicating a tip to the end recognized as the tip among the both ends including one end and the other end in the image shown in (a) of FIG. 5, and outputs the attached information to presentation device 21. Note that orientation identifying unit 12b may &so generate, as information indicating the identified orientation, a vector from the root toward the tip of a body hair, using the slope of a long side of a bounding box.

In this way, the orientation of each body hair in the image is identified from the captured image as practical information about body hair. Therefore, a user who has obtained this practical information can immediately know in which direction unshaved body hair should be shaved so that the unshaved body hair can be shaved efficiently and cleanly,

[3. Effects, Etc.]

As described above, image processing device 10 according to the present embodiment includes: obtaining unit 11 configured to obtain an image including at least one body hair; and analyzing unit 12 configured to analyze the image to output information indicating an orientation of the at least one body hair included in the image.

With this, the orientation of each body hair in the image is identified from the captured image as practical information about body hair. For example, since the orientation of each body hair left unshaved by an electric razor can be known, it is possible to immediately know in which direction each unshaved body hair should be shaved so that each unshaved body hair can be shaved efficiently and cleanly.

Moreover, analyzing unit 12 is configured to recognize at least one of a root or a tip of the at least one body hair included in the image. To achieve this, analyzing unit 12 is configured to analyze a change in luminance at each of both ends including one end and the other end of the at least one body hair included in the image, and determine that an end having a larger change in luminance among the both ends is the tip of the at least one body hair. With this, the orientation of the body hair is identified highly accurately using features of the root and the tip of the body hair in the image.

Moreover, analyzing unit 12 is configured to analyze a change in luminance at the one end and the other end of the at least one body hair using a high-pass filter, and recognize an end having a larger value obtained by applying the high-pass filter among the both ends as the tip of the at least one body hair. In this way, the root and the tip of each body hair are reliably identified with a simple process, and the orientation of the root of the body hair is determined highly accurately.

Moreover, analyzing unit 12 is further configured to identify the length of the at least one body hair included in the image, and output information indicating the length identified. This provides information about not only the orientation of each body hair, but also the length of each body hair, as more practical information about body hair. Therefore, for example, capturing an image of body hair left unshaved by an electric razor makes it possible to immediately know which part on the body should be further shaved in preference to other parts so that the unshaved body hair can be shaved efficiently and cleanly.

Moreover, analyzing unit 12 is configured to perform, on the image, a process of enhancing contrast, a process of extracting an outline of the at least one body hair, and a process of calculating a bounding box to identify the length of the at least one body hair. In this way, the length of each body hair is reliably identified.

Moreover, analyzing unit 12 is configured to identify the orientation of the at least one body hair in an area enclosed by the bounding box in the image on which the process of calculating the bounding box has been performed. This makes it possible to use the bounding box calculated for the length of the body hair also for identifying the orientation of the body hair. Therefore the orientation of the body hair is determined with a small processing load.

Moreover, an image processing method according to the present embodiment includes: obtaining an image including at least one body hair by obtaining unit 11; and analyzing the image to output information indicating an orientation of the at least one body hair included in the image by analyzing unit 12.

With this, the orientation of each body hair in the image is identified from the captured image as practical information about body hair. For example, since the orientation of each body hair that is left unshaved by an electric razor can be known, it is possible to immediately know in which direction each unshaved body hair should be shaved so that each unshaved body hair can be shaved efficiently and cleanly.

Other Embodiments

As described above, the embodiment has been described above as an example of the technique disclosed in the present application. However, this is not limiting. Changes, replacements, additions, and omissions can be made in the embodiment as appropriate. It is also possible to combine the structural elements described in the above embodiment to create a new embodiment.

Therefore, other embodiments will be collectively described below.

For example, in the above embodiment, obtaining unit 11 obtains an image including at least one body hair from camera 20. However, obtaining unit 11 is not limited to this. Obtaining unit 11 may obtain an image from a device, for example, a storage such as memory or a hard disk drive (HDD) that stores images and is provided externally or internally, or from a server device connected through communication such as the Internet.

Moreover, in the above embodiment, the operation of image processing device 10 has been described using an image obtained by capturing the unshaved beard in FIG. 3 as an example. However, examples of body hair include not only an unshaved beard, but also any hair that grows on any part on body, such as chest hair, leg hair, down hair, and head hair.

Moreover, in the above embodiment, analyzing unit 12 includes both length identifying unit 12a and orientation identifying unit 12b, but may include only orientation identifying unit 12b. With this, the orientation of each body hair in the image is identified from the captured image, as practical information about body hair. Therefore, for example, since the orientation of each body hair that is left unshaved by an electric razor can be known, it is possible to immediately know in which direction each body hair should be shaved so that each unshaved body hair can be shaved efficiently and cleanly.

Moreover, in the above embodiment, analyzing unit 12 includes both length identifying unit 12a and orientation identifying unit 12b, but may include only length identifying unit 12a. With this, the length of each body hair in the image is identified from the captured image, as practical information about body hair. Therefore, for example, since the length of each body hair that is left unshaved by an electric razor can be known, it is possible to immediately know which part on the body should be shaved in preference to other parts so that each unshaved body hair can be shaved efficiently and cleanly.

Moreover, in the above embodiment, a microcomputer has been described as an example of analyzing unit 12. If a programmable microcomputer is used as part of analyzing unit 12, the processing can be changed by changing the program, thereby increasing the degrees of freedom in the design of analyzing unit 12. Analyzing unit 12 may also be achieved by a hard logic. If analyzing unit 12 is achieved by hard-wired logic, it is effective for improving processing speed. Analyzing unit 12 may include a single element or multiple physical elements. In the case of including multiple elements, each control (length identifying unit and orientation identifying unit) described in the claims may be achieved by another element. In this case, it can be considered that these multiple elements are included in a single analyzing unit 12, It is also possible to achieve analyzing unit 12 by including a single element having a function different from analyzing unit 12. In short, analyzing unit 12 may be physically constructed in any way as long as analyzing unit 12 can process images.

In addition, the technique according to the present disclosure may be achieved not only as an image processing device and an image processing method, but also as a program that causes a computer to execute the steps included in the image processing method, or as a non-transitory computer-readable recording medium such as a CD-ROM having the program recorded thereon.

As described above, the embodiment has been described above as an example of the technique disclosed in the present disclosure. For this purpose, accompanying drawings and detailed description are provided. Therefore, the structural elements in the detailed description and the accompanying drawings may include not only the structural elements essential for the solution of the problem but also the structural elements not essential for the solution of the problem, to illustrate the above implementation. Therefore, the inclusion of such optional structural elements in the detailed description and the accompanying drawings therefore does not mean that these optional structural elements are essential structural elements.

The foregoing embodiment is intended to be illustrative of the disclosed technique, and therefore various changes, replacements, additions, omissions, etc, can be made within the scope of the appended claims and their equivalents.

INDUSTRIAL APPLICABILITY

The present disclosure is applicable to an image processing device that can provide practical information about body hair. Specifically, the present disclosure is applicable to, for example, a computer device and a smartphone that obtain and analyzes image from a digital camera.

REFERENCE SIGNS LIST 10 image processing device
11 obtaining unit 12 analyzing unit
12a length identifying unit
12b orientation identifying unit
20 camera
21 presentation device
The invention claimed is:

1. An image processing device comprising:
an obtaining unit configured to obtain an image including at least one body hair; and
an analyzing unit configured to analyze the image, wherein
the analyzing unit is configured to output information indicating an orientation of the at least one body hair included in the image, and
the analyzing unit is configured to analyze a change in luminance at each of both ends including one end and an other end of the at least one body hair included in the image, and determine, among the both ends, at least one of a root or a tip of the at least one body hair included in the image based on the change in luminance.

2. The image processing device according to claim 1, wherein
the analyzing unit is configured to determine that an end having a larger change in luminance among the both ends is the tip of the at least one body hair.

3. The image processing device according to claim 2, wherein
the analyzing unit is configured to analyze a change in luminance at the one end and the other end of the at least one body hair using a high-pass filter, and recognize an end having a larger value obtained by applying the high-pass filter among the both ends as the tip of the at least one body hair.

4. The image processing device according to claim 1, wherein
the analyzing unit is further configured to identify a length of the at least one body hair included in the image, and output information indicating the length identified.

5. The image processing device according to claim 4, wherein
the analyzing unit is configured to perform, on the image, a process of enhancing contrast, a process of extracting an outline of the at least one body hair, and a process of calculating a bounding box to identify the length of the at least one body hair.

6. The image processing device according to claim 5, wherein
the analyzing unit is configured to identify the orientation of the at least one body hair in an area enclosed by the bounding box in the image on which the process of calculating the bounding box has been performed.

7. An image processing method comprising:
obtaining an image including at least one body hair;
analyzing the image to output information indicating an orientation of the at least one body hair included in the image; and
analyzing a change in luminance at each of both ends including one end and an other end of the at least one body hair included in the image, and determining, among the both ends, at least one of a root or a tip of the at least one body hair included in the image based on the change in luminance.

* * * * *